US 8,523,795 B2

(12) United States Patent
McCune et al.

(10) Patent No.: US 8,523,795 B2
(45) Date of Patent: Sep. 3, 2013

(54) ARM SLING WITH BACKPACK STRAPS

(75) Inventors: Robert J. McCune, Escalon, CA (US); Jeffrey L. Telles, Tracy, CA (US)

(73) Assignee: Top Shelf Manufacturing, LLC, Stockton, CA (US)

( * ) Notice: Subject to any disclaimer, the term of this patent is extended or adjusted under 35 U.S.C. 154(b) by 0 days.

(21) Appl. No.: 13/316,911

(22) Filed: Dec. 12, 2011

(65) Prior Publication Data

US 2012/0150083 A1    Jun. 14, 2012

Related U.S. Application Data

(60) Provisional application No. 61/421,664, filed on Dec. 10, 2010.

(51) Int. Cl.
*A61F 5/00* (2006.01)
(52) U.S. Cl.
USPC ............................................. 602/4
(58) Field of Classification Search
USPC .................. 602/4–5, 20–23; 128/878–879
See application file for complete search history.

(56) References Cited

U.S. PATENT DOCUMENTS

| 195,941 | A | * | 10/1877 | McCabe | 602/4 |
| 1,304,153 | A | * | 5/1919 | Bugge | 602/4 |
| 1,808,422 | A | * | 6/1931 | MacDonald | 602/4 |
| 2,111,963 | A | * | 3/1938 | Coombs | 602/4 |
| 2,796,862 | A | * | 6/1957 | Borntraeger | 602/4 |
| 4,372,301 | A | | 2/1983 | Hubbard | |
| 4,598,701 | A | | 7/1986 | Schaefer | |
| 4,622,961 | A | | 11/1986 | Christensen | |
| 4,834,082 | A | | 5/1989 | Ghadiali | |
| 5,141,488 | A | | 8/1992 | Schrader | |
| 7,037,281 | B1 | * | 5/2006 | Jeffrey et al. | 602/4 |
| 7,563,236 | B2 | | 7/2009 | Kazmierczak | |
| 7,789,842 | B2 | | 9/2010 | Bittar | |

* cited by examiner

*Primary Examiner* — Michael A. Brown
(74) *Attorney, Agent, or Firm* — Dickstein Shapiro LLP

(57) ABSTRACT

A sling with straps configured in a manner similar to those of a backpack. The sling includes a waist strap connected at one end to an anterior portion of the sling pouch and at a second end to a posterior second portion of the sling pouch. The sling include first and second straps that are worn over respective shoulders of the body. One of the straps is connected at one end a first end of the pouch and at an opposite end to a second (opposite) end of the pouch. The second strap is connected at one end to the first end of the pouch and at an opposite end to the waist strap. The sling can also include an abduction pillow.

21 Claims, 7 Drawing Sheets

ARM SLING WITH BACKPACK STRAPS

CROSS-REFERENCE TO RELATED APPLICATIONS

This application claims the benefit of U.S. Provisional Application No. 61/421,664, filed on Dec. 10, 2010.

BACKGROUND OF THE INVENTION

1. Field of the Invention

The present invention is directed to an arm sling with backpack straps for treatment of a patient's shoulder, arm, or wrist which provides distribution of pressures caused by use and can provide abduction.

2. Description of the Related Art

Various types of arm slings are known for use in supporting an arm during the healing process in the treatment of injuries to the shoulder or the arm and wrist. Slings are used to hold the shoulder, arm, or wrist in place and to restrict movement by the shoulder, arm, or wrist, such that healing occurs. Simple slings comprise a pouch and a strap connected to the pouch, wherein the strap loops around the neck of the patient to support the pouch. The patient's forearm rests in the pouch. U.S. Pat. Nos. 4,372,301, 4,622,961, and 4,834,082 are examples of these types of simple shoulder slings.

In a typical arm sling, the patient's neck supports all of the weight of the supported arm, often causing discomfort to the patient. The strap also can rub the patient's neck, adding to the patient's discomfort.

Slings have evolved over the years to not only provide the function of supporting an immobilized arm, but also to provide abduction. U.S. Pat. Nos. 7,563,236 and 4,598,701 disclose slings which provide abduction.

However, known slings, including those disclosed in the aforementioned patents, which provide abduction and support do not provide load sharing such that the weight of the arm in the pouch is distributed in a more comfortable manner for the patient.

Furthermore, while abduction pillows exist, there exists a need for an abduction pillow that also provides pressure relief of the distal humerus. Abduction pillows can be used in conjunction with slings to support the patient's arm at a desired abduction angle. However, the design of past abduction pillows can exert pressure upon the distal humerus of the patient.

Therefore, it would be desirable to provide a shoulder or arm sling which can be used to treat injuries by restricting movement and providing abduction, while at the same time providing the patient with a more comfortable experience.

SUMMARY OF THE INVENTION

In one form, the present disclosure provides a sling including a pouch having a first end and a second end opposite the first end. The sling also includes a waist strap having a first end connected to the first end of the pouch and a second end connected the second end of the pouch, a first strap having a first end connected to the first end of the pouch and a second end connected to the second end of the pouch, and a second strap having a first end connected to the first end of the pouch and a second end connected to the waist strap.

In another form, the present disclosure provides a sling including an abduction pillow, a pouch connected to the abduction pillow, a waist strap having a first end and a second end, a first strap having a first end and a second end, and a second strap having a first end and a second end. The abduction pillow and the pouch form an assembly having a first portion and a second portion opposite the first portion. The first end of the waist strap is connected to the first portion of the assembly and the second end of the waist strap is connected to the second portion of the assembly. The first end of the first strap is connected to the first portion of the assembly and the second end of the first strap is connected to the second portion of the assembly. The first end of the second strap is connected to the first portion of the assembly and the second end of the second strap is connected to the waist strap.

In another form, the present disclosure provides an arm sling including an abduction pillow having an anterior portion and a posterior portion and a pouch connected to the abduction pillow. The arm sling also includes a waist strap having a first end connected to the anterior portion of the abduction pillow and a second end connected the posterior second portion of the abduction pillow. The arm sling further includes a first strap having a first end connected to the anterior portion of the abduction pillow and a second end connected to the posterior portion of the abduction pillow, and a second strap having a first end connected to the anterior portion of the abduction pillow and a second end connected to the waist strap.

BRIEF DESCRIPTION OF THE DRAWINGS

FIG. 6 is a front view of a third embodiment of the present invention as worn by a patient; and.

DETAILED DESCRIPTION OF THE PREFERRED EMBODIMENTS

The following description is provided to enable any person skilled in the art to make and use the invention and sets forth the best modes contemplated by the inventors of carrying out their inventions. Various modifications, however, will remain readily apparent to those skilled in the art, since the general principles of the present invention have been defined herein to specifically provide a stable sling backpack.

Figure 1:
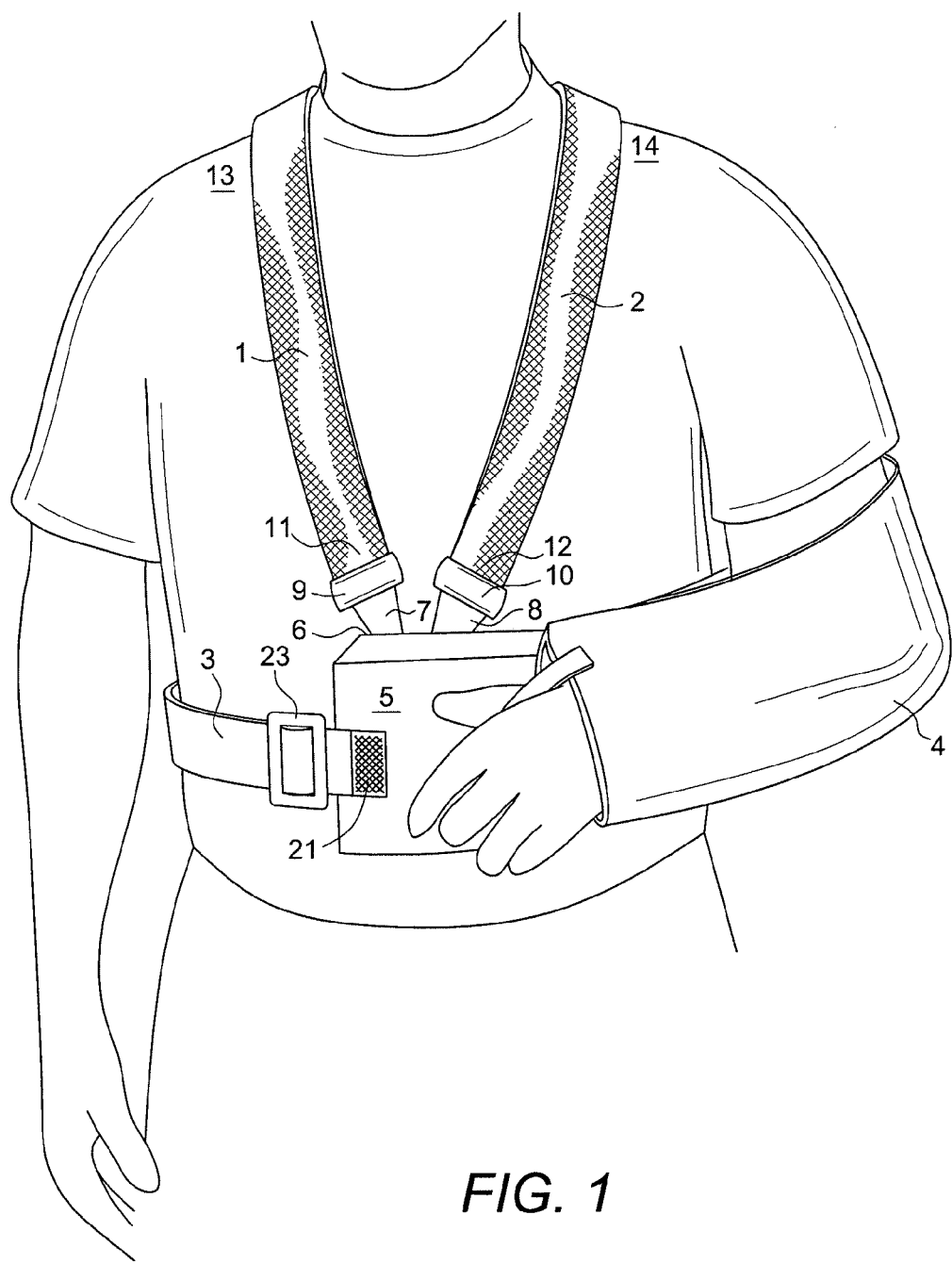
FIG. 1 is a front view of the sling of the present invention as worn by a patient.
Figure 2:
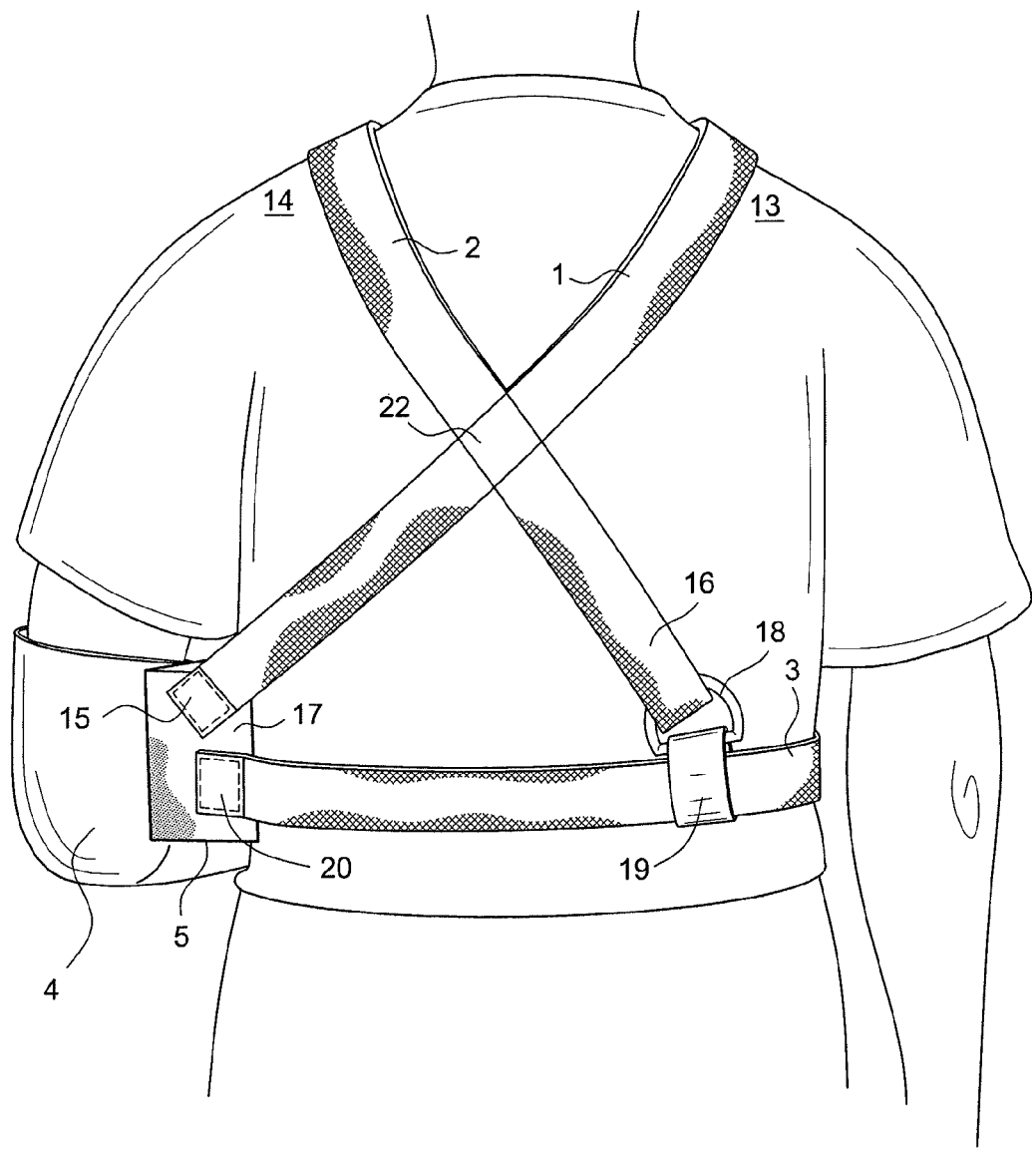
FIG. 2 is a back view of the sling of the present invention as worn by a patient.

The present invention, shown in FIGS. 1 and 2, is a stable arm sling with backpack configured straps which provides restriction of movement and abduction for the healing of an arm or shoulder and which also evenly distributes the weight of the arm onto a user's shoulders. The weight of the arm is distributed by load sharing. As can be seen in FIG. 1, the sling includes a first strap 1, a second strap 2, a waist strap 3, a pouch 4, and an abduction pillow 5. The first end 11 of the first strap 1 is connected to the anterior end 6 of the abduction pillow 5 via connecting member 9 and connection point 7. The first end 12 of the second strap 2 is connected to the anterior end 6 of the abduction pillow 5 via connecting member 10 and connection point 8. The pouch 4 is connected laterally to the abduction pillow 5. The first end 21 of the waist strap 3 is connected to the abduction pillow 5. The patient's arm is placed into the pouch 4, such that the patient's arm, shoulder, or wrist is supported.

The first strap 1 extends over the first shoulder 13 of the patient. As shown in FIG. 2, the first strap 1 extends diagonally from the first shoulder 13 over the back of the patient, such that the second end 15 of the first strap 1 attaches to the posterior end 17 of the abduction pillow 5, near the patient's elbow. The second strap 2 extends over the second shoulder 14 of the patient. The second strap 2 extends diagonally from the second shoulder 14 over the back of the patient, such that the second end 16 of the second strap 2 attaches to the waist strap 3 via connecting member 18 at connection point 19. Connection point 19 can be movable along the waist strap 3, and can be secured at a desired position. This allows the second strap 2 to attach to the waist strap 3 at various positions. The second end 20 of the waist strap 3 is attached to the posterior end 17 of the abduction pillow 5. The first strap 1 and second strap 2 cross-over the patient's back at point 22 and, while not required, first strap 1 and second strap 2 can be optionally connected to each other at cross-over point 22.

The sling can be adjusted to fit patients of all sizes. As shown in FIG. 1, the waist strap 3 is adjustable via mechanism 23. The first strap 1 and second strap 2 are also adjustable to fit patients of all sizes. Adjustment of the length of the first and second straps 1, 2 can be accomplished, for example, by using hook-and-loop material to lengthen or shorten the straps. As discussed above, connection point 19 can be movable along the waist strap, which allows the sling to be further adjusted to fit the patient. In addition to fitting the sling to patients of different sizes, adjusting the first shoulder strap 1, second shoulder strap 2, and waist strap 3 also allows the abduction pillow 5 and the arm pouch 10 to be secured such that the shoulder, arm, or wrist are secured at various positions.

The abduction pillow 5 is secured to the body of the patient with the waist strap 3 and first 1 and second straps 2. This allows load to be shared between the three straps. Furthermore, because the sling is connected laterally to the pillow, the downward force is greatly reduced, thereby decreasing the load on the first strap 1 and second strap 2 that pass over the patient's shoulder. Thus, a stable sling backpack which provides load sharing is presented.

Figure 3:
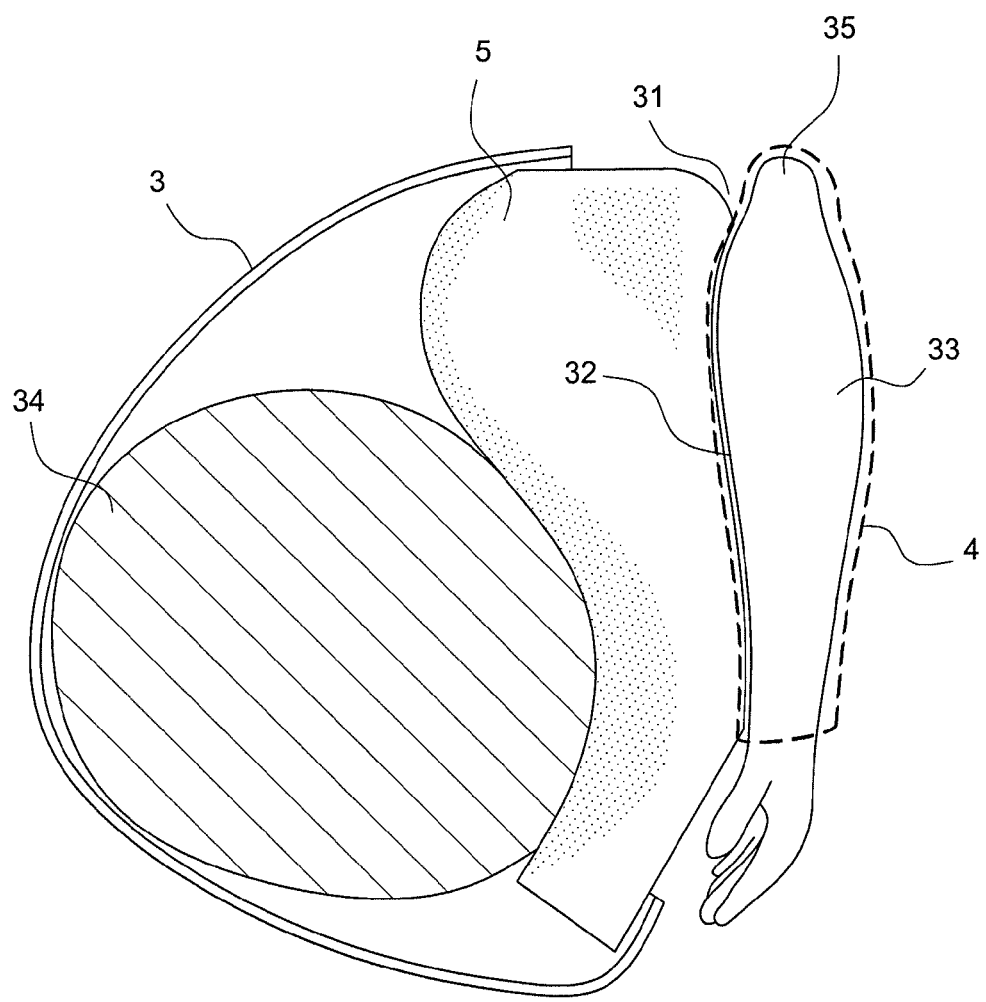
FIG. 3 is a top view of a patient wearing the sling of the present invention.
Figure 4:
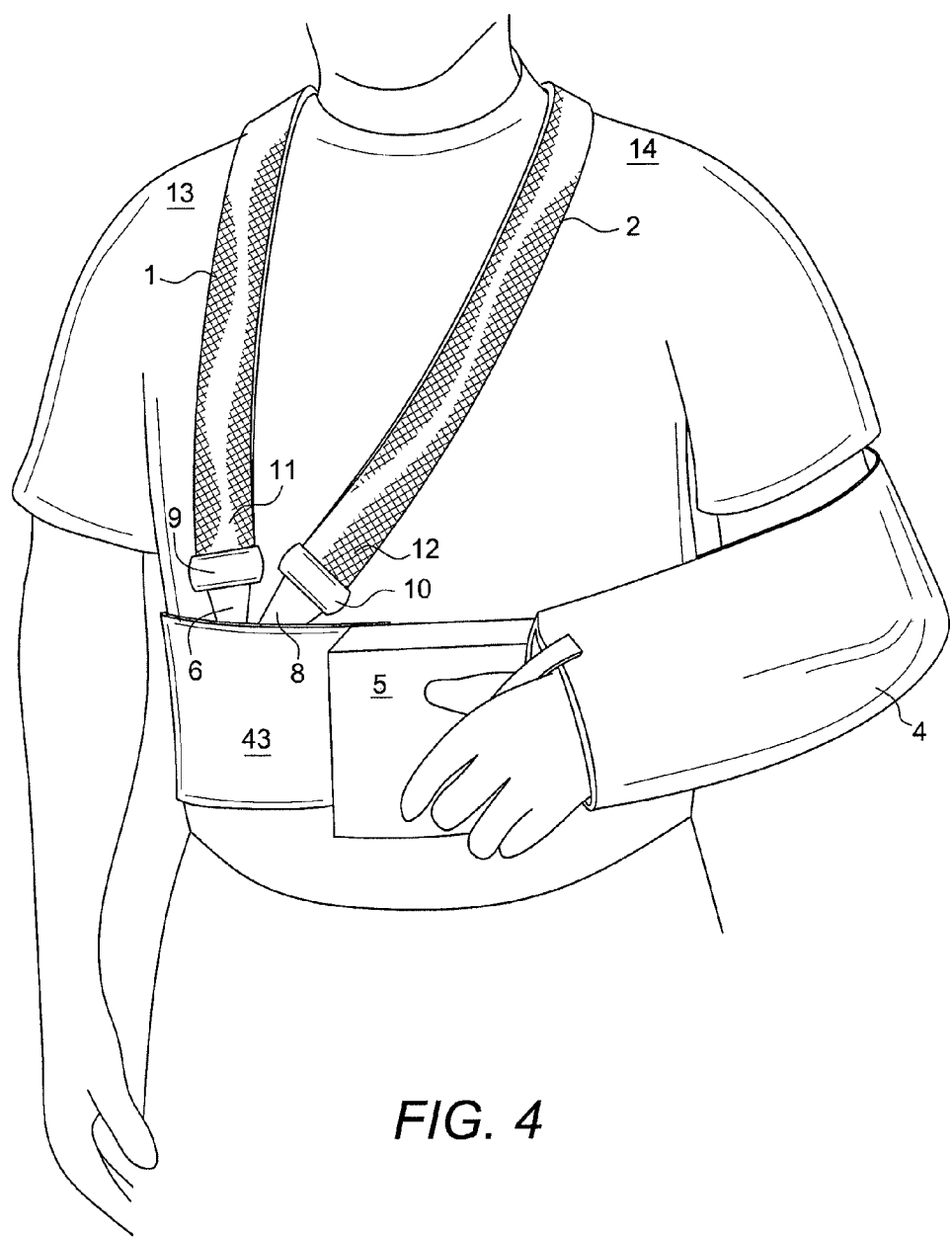
FIG. 4 is a front view of a second embodiment of the present invention as worn by a patient.

Additionally, the stable sling backpack can be used with an improved abduction pillow FIG. 3 provides a top-down view of a patient using an embodiment of the improved abduction pillow 5. As shown, the abduction pillow 5 is placed between the patient's body 34 and the patient's arm 33, and the arm is placed into the sling's pouch 4. The abduction pillow 5 is secured to the patient's body by using a waist strap 3 as well as a first strap 1 (not pictured in FIG. 3) and a second strap 2 (not pictured in FIG. 3). The sling's pouch 4 is secured to the outer edge 32 of the abduction pillow 5. The pouch 4 can be secured to the abduction pillow 5 at the pillow's outer edge 32 by permanent means or by releasable means. In this configuration, the patient's arm is supported at an abduction angle. The posterior end of the abduction pillow is cut-out 31, or directed away from, the patient's distal humerus 35. Thus, the abduction pillow does not press against the patient's distal humerus 35 and does not create pressure on the distal humerus 35.

Those skilled in the art will appreciate that adoptions and modifications of the just-described preferred embodiment can be configured without departing from the scope and spirit of the invention. For example, the second end 15 of first strap 1 can be attached to the pouch 4, rather than to the posterior end 17 abduction pillow 5, as disclosed in the first embodiment. Furthermore, the stable sling backpack can perform load sharing without the abduction pillow 5. Another potential modification allows for different methods and mechanisms to adjust strap length and size to resize the sling. Yet another modification includes the abduction pillow 5 optionally comprising dual density foam. While the drawings show a stable sling backpack for the left-arm, the sling of the present invention can obviously be configured for right-arm use as well.

Figure 5:
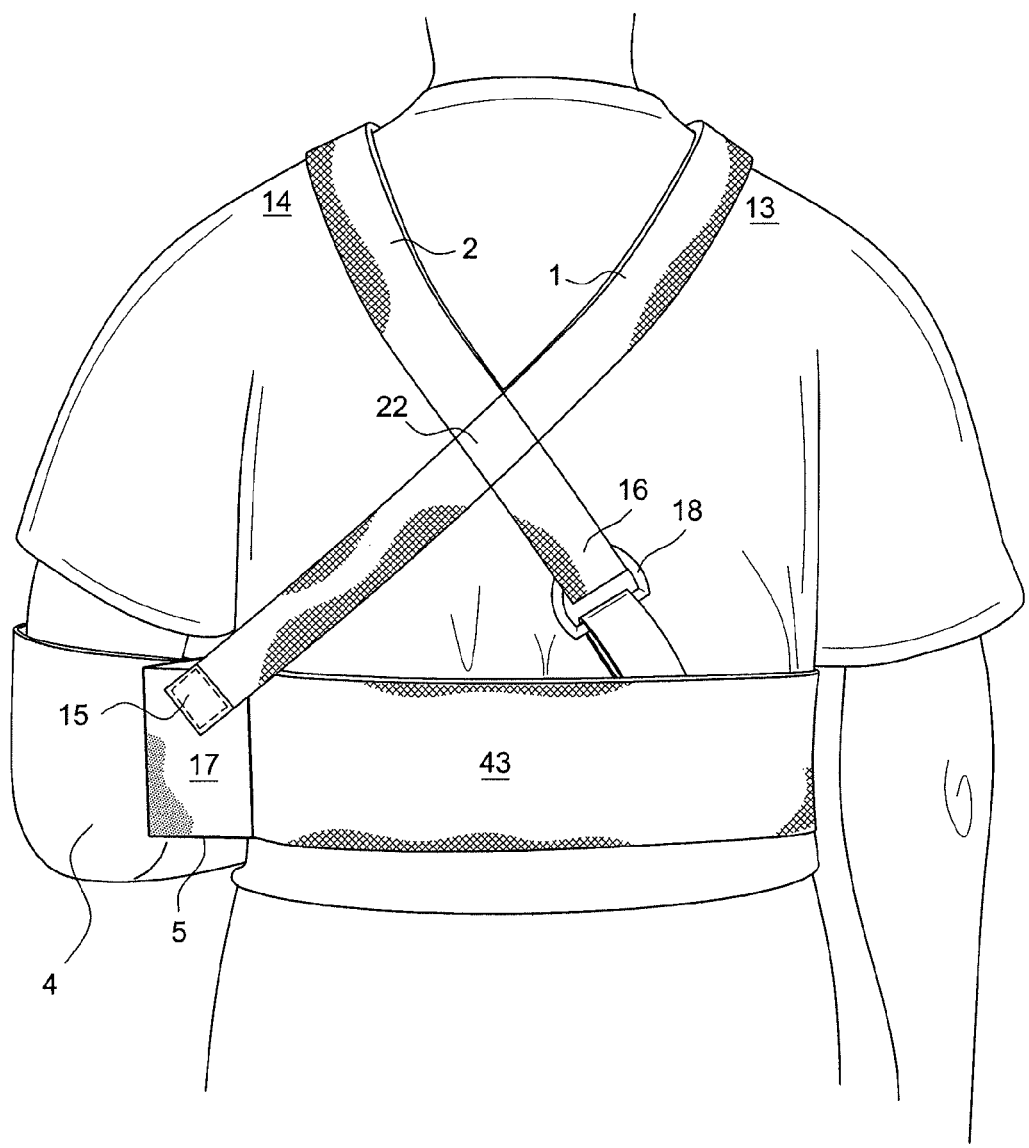
FIG. 5 is a back view of the sling of the second embodiment of the present invention.
Figure 6:
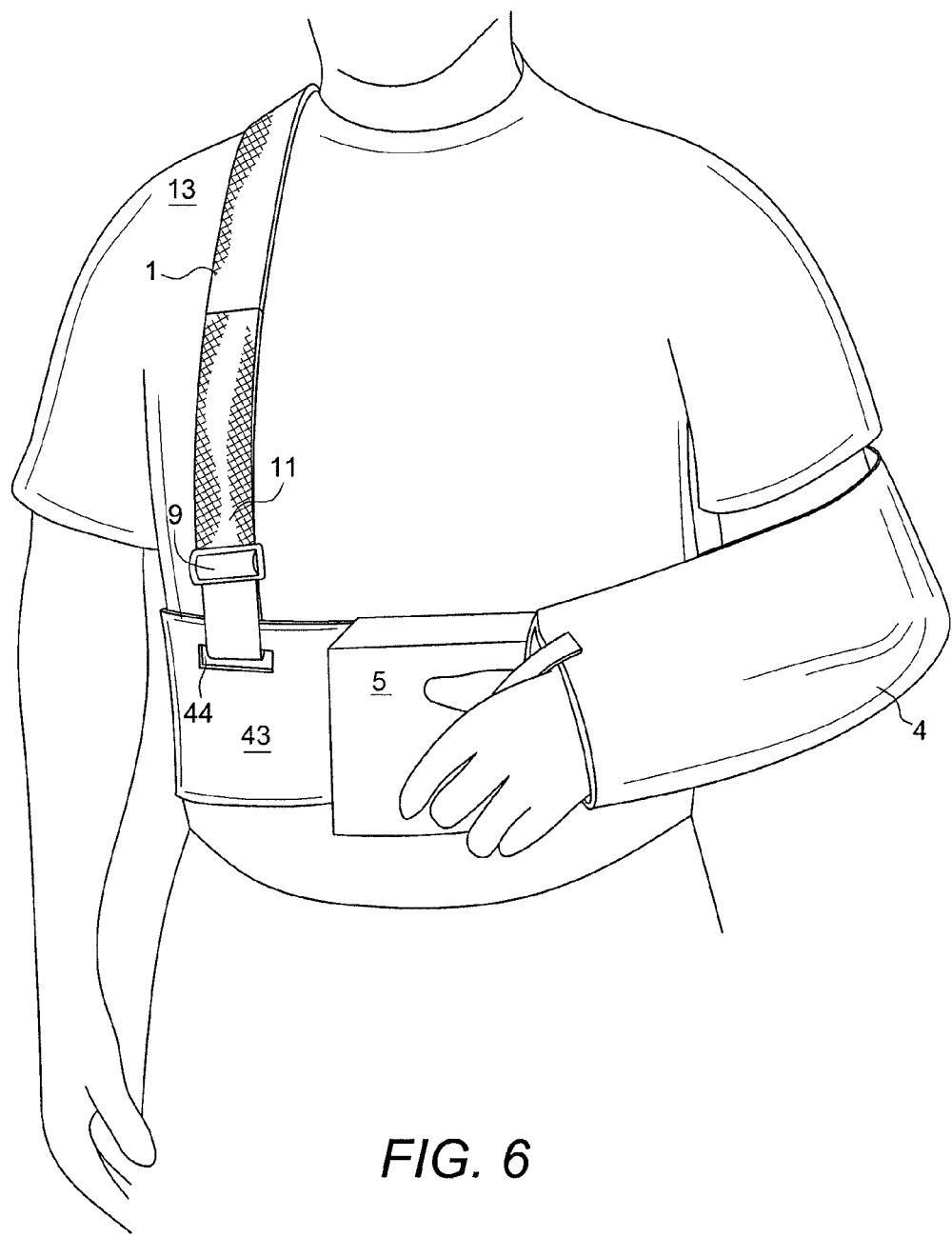
Figure 7:
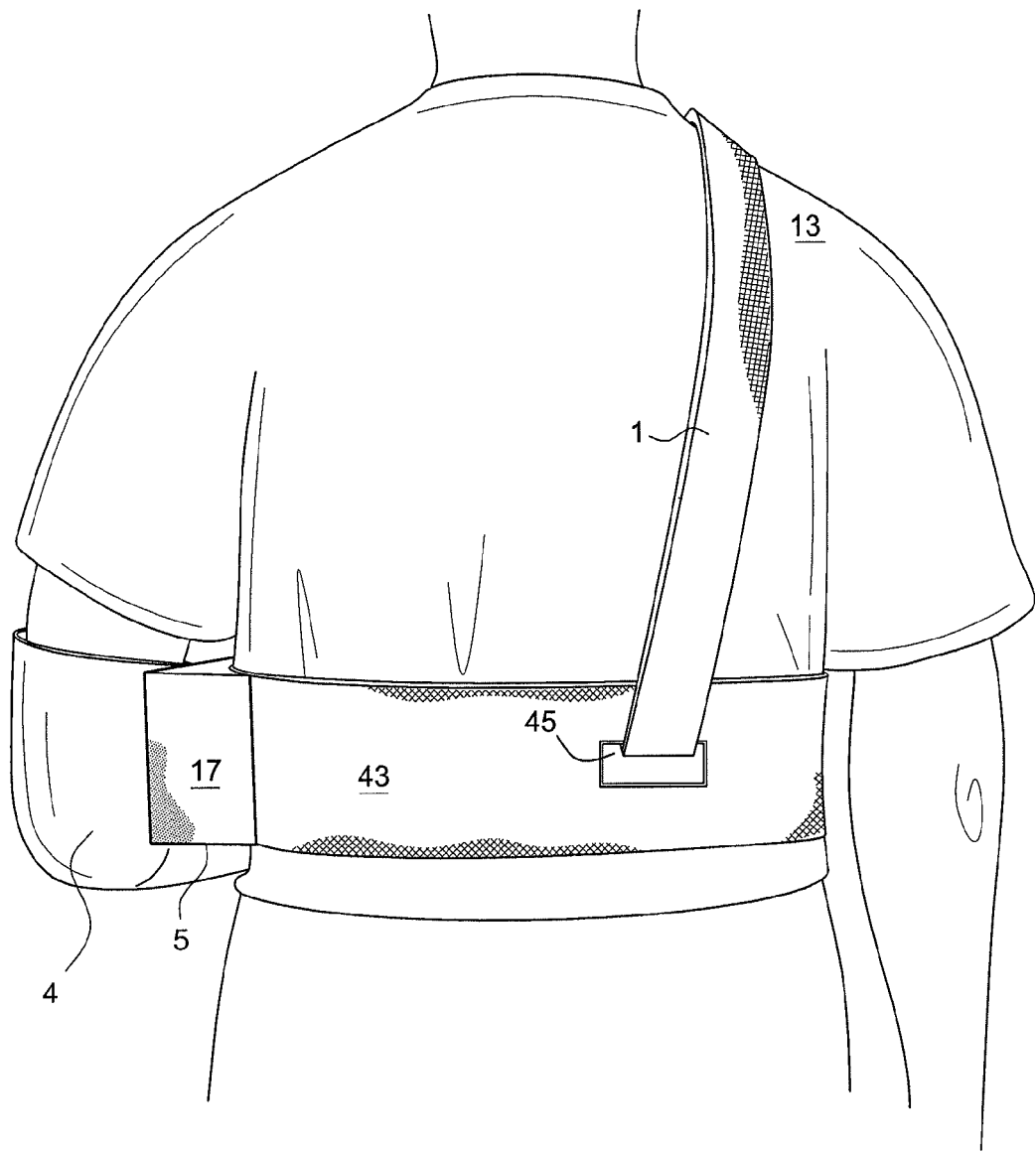
FIG. 7 is a back view of the sling of the third embodiment of the present invention.

A further embodiment of the invention is shown in FIGS. 5 and 6, wherein like reference numerals indicate like elements from the first embodiment, the belt 43 is wider than belt 3 of the first embodiment, such that belt 43 is essentially the same width as pillow 5 and is integrated with the pillow. A still further embodiment of the invention is shown in FIGS. 7 and 8, in which the wide belt 43 integrated with the pillow has a front slot 44 and a back slot 45 for attachment of a single shoulder strap 1, which simply rests on the shoulder 13 of the patient without crossing over another strap on the patient's back.

The above description and drawings illustrate preferred embodiments which achieve the objects, features and advantages of the present invention. It is not intended that the present invention be limited to the illustrated embodiments, but rather only by the appended claims.

What is claimed is:

1. A sling, comprising:
 a pouch having a first end and a second end opposite said first end;
 an abduction pillow connected to said pouch;
 a waist strap having a first end connected to said first end of said pouch and a second end connected said second end of said pouch;
 a first strap having a first end connected to said first end of said pouch and a second end connected to said second end of said pouch; and
 a second strap having a first end connected to said first end of said pouch and a second end connected to said waist strap.

2. The sling of claim 1, wherein said first strap and said second strap cross one another and are fixed together at the crossing point.

3. The sling of claim 1, wherein the attachment point of said second end of said second strap to said waist strap is movable along the length of said waist strap.

4. The sling of claim 1, wherein the length of said waist strap, said first strap, and said second strap is adjustable.

5. A sling, comprising:
 an abduction pillow;
 a pouch connected to said abduction pillow;
 a waist strap having a first end and a second end;
 a first strap having a first end and a second end; and
 a second strap having a first end and a second end, wherein:
  said abduction pillow and said pouch form an assembly having a first portion and a second portion opposite said first portion;
  said first end of said waist strap is connected to said first portion of said assembly and said second end of said waist strap is connected to said second portion of said assembly;
  said first end of said first strap is connected to said first portion of said assembly and said second end of said first strap is connected to said second portion of said assembly; and
  said first end of said second strap is connected to said first portion of said assembly and said second end of said second strap is connected to said waist strap.

6. The sling of claim 5, wherein:
 said first portion of said assembly is an anterior end of said assembly; and said second portion of said assembly is posterior end of said assembly.

7. The sling of claim 6, wherein said first strap and said second strap cross one another and are fixed together at the crossing point.

8. The sling of claim 7, wherein the attachment point of said second end of said second strap to said waist strap is movable along the length of said waist strap.

9. The sling of claim 6, wherein a portion of said abduction pillow adjacent said pouch at said posterior end of said assembly is cut out away from said pouch.

10. The sling of claim 6, wherein the length of said waist strap, said first strap, and said second strap is adjustable.

11. The sling of claim 10, wherein said pouch is releasably connected to said abduction pillow.

12. The sling of claim 10, wherein said pouch is permanently connected to said abduction pillow.

13. The sling of claim 10, wherein said pouch is constructed from dual density foam.

14. An arm sling, comprising:
   an abduction pillow having an anterior portion and a posterior portion;
   a pouch connected to said abduction pillow;
   a waist strap having a first end connected to said anterior portion of said abduction pillow and a second end connected said posterior second portion of said abduction pillow;
   a first strap having a first end connected to said anterior portion of said abduction pillow and a second end connected to said posterior portion of said abduction pillow; and
   a second strap having a first end connected to said anterior portion of said abduction pillow and a second end connected to said waist strap.

15. The arm sling of claim 14, wherein the length of said waist strap, said first strap, and said second strap is adjustable.

16. The arm sling of claim 14, wherein said first strap and said second strap cross one another and are fixed together at the crossing point.

17. The arm sling of claim 15, wherein the attachment point of said second end of said second strap to said waist strap is movable along the length of said waist strap.

18. The arm sling of claim 17, wherein said pouch is releasably connected to said abduction pillow.

19. The arm sling of claim 18, wherein a posterior portion of said abduction pillow adjacent said pouch is cut out away from said pouch.

20. A sling, comprising:
   a pouch having a first end and a second end opposite said first end;
   a waist strap integrated with the pouch and having a first end connected to said first end of the pouch and a second end connected to the second end of the pouch;
   a first strap having a first end connected to said first end of said waist strap and a second end connected to another portion of said waist strap, wherein the first strap is connected to the waist strap by passing through respective slots in the waist strap.

21. The sling of claim 20, further comprising a second strap having a first end connected to said first end of said waist strap and a second end connected to the second end of the pouch.

* * * * *